United States Patent [19]

Carroll et al.

[11] Patent Number: 5,169,786
[45] Date of Patent: Dec. 8, 1992

[54] METHOD OF DETERMINING LEVELS OF EXTRINSIC AND INTRINSIC CLOTTING FACTORS AND PROTEIN C

[75] Inventors: James J. Carroll, East Hanover; Stephen M. Autenrieth, Bernardsville, both of N.J.

[73] Assignee: Ortho Diagnostic Systems, Inc., Raritan, N.J.

[21] Appl. No.: 452,802

[22] Filed: Dec. 19, 1989

[51] Int. Cl.[5] .......................................... G01N 33/16
[52] U.S. Cl. .................................. 436/69; 436/34; 436/164; 436/517; 436/805; 436/809; 435/13
[58] Field of Search .................. 436/69, 63, 34, 166, 436/164, 86, 511, 805, 809; 435/13

[56] References Cited

U.S. PATENT DOCUMENTS

| | | | |
|---|---|---|---|
| 3,307,392 | 3/1967 | Owen et al. | 73/64.1 |
| 3,458,287 | 7/1969 | Gross et al. | 23/230 |
| 3,658,480 | 4/1972 | Kane et al. | 23/230 |
| 4,047,890 | 9/1977 | Eichelberger et al. | 23/230 B |
| 4,289,498 | 9/1981 | Baughman et al. | 23/230 B |
| 4,766,083 | 8/1988 | Miyashita et al. | 436/517 |

OTHER PUBLICATIONS

Ortho Factor VIII:C Deficient Plasma Ortho Diagnostic Systems Inc. 1988.
American Diagnostica Inc. 3X15 Test Kit for Determination of Plasma Protein C Activity Using a Clotting End-Point.
Package insert for Ortho Brain Thromboplastic Reagent.
Package insert for Ortho's Activated Thrombofax Reagent.
The American Society of Hematology 31st Annual Meeting Abstract Reproduction Form.
American Clinical Laboratory (Apr. 1989).
The Clot Signature and New Aspects in Coagulation Testing Ortho Diagnostic Systems Inc. (Aug. 1989).

Primary Examiner—James C. Housel
Assistant Examiner—David Redding
Attorney, Agent, or Firm—Woodcock Washburn Kurtz Mackiewicz & Norris

[57] ABSTRACT

A method of determining levels of extrinsic and intrinsic clotting factors and protein C based upon the reaction rate of the observed clot formation and the first derivative of the reaction rate of observed clot formation is provided. In accordance with the teachings of the invention, the reaction rate of the observed clot formation in a prothrombin time test or an activated partial thromboplastin time assay is determined for both test and normal plasma samples and the reaction rates compared. In another embodiment, the first derivative of the reaction rate of the observed clot formation is determined and the results compared.

18 Claims, 7 Drawing Sheets

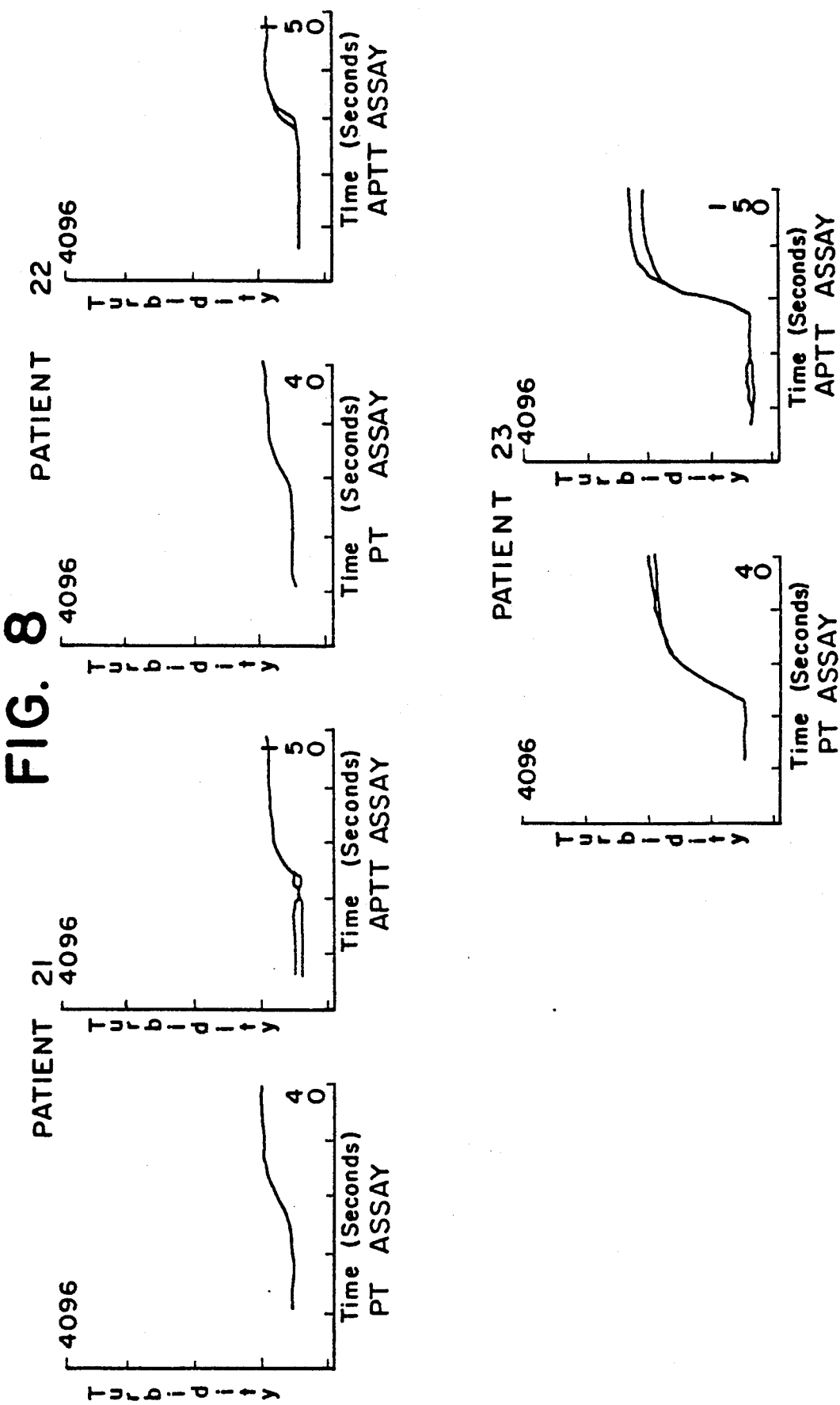

METHOD OF DETERMINING LEVELS OF EXTRINSIC AND INTRINSIC CLOTTING FACTORS AND PROTEIN C

FIELD OF THE INVENTION

The invention relates to a method of determining levels of extrinsic and intrinsic clotting factors and protein C based upon the reaction rate of the observed clot formation and the first derivative of the reaction rate of observed clot formation.

BACKGROUND OF THE INVENTION

Clotting of blood is a complicated process involving a large number of blood components including fibrinogen and prothrombin which is converted to thrombin. It has long been recognized that many aspects of unexplained bleeding or abnormal clotting can be explained in terms of improper levels of these materials in the blood. For instance, states of hypo-fibrinogenemia or hyper-fibrinogenemia may result from hepatic disease, from disseminated intravascular coagulation, from fibrinolytic syndrome, neoplastic disease, and post-operatively due to trauma. By monitoring the fibrinogen, thrombin and prothrombin levels within the blood, a physician may acquire meaningful data concerning the patient's blood clotting abilities. For example, the Activated Partial Thromboplastin Time (APTT) Test measures coagulation factors of the intrinsic pathway. These factors include Factors XII, XI, IX, VIII, X, V, II and I which may be abnormal based on heredity or heparin therapy. Thus, the APTT test is useful as a presurgical screen and for monitoring heparin therapy. Similarly, fibrinogen testing (by the Thrombin Time (TT) test or quantitative fibrinogen test) provides useful diagnostic data when unexplained bleeding or abnormal clotting occurs.

Within the past decade, evidence has accumulated linking soluble clotting factors with ischemic heart disease. Studies have shown that elevated blood plasma concentrations of Factors VIIa, VIIIc, and fibrinogen appear to be associated with an increased risk of heart attack and cardiovascular death. Patients who are in such a hypercoagulable state require careful monitoring. In the past, decisions to change medication, adjust dosage, or proceed with surgery were made based upon clotting time.

The process of blood coagulation occurs as a series of complex steps which terminate in the formation of a fibrin clot. Clot formation may occur by activation of the intrinsic pathway. In this system, coagulation factors circulate in the form of inactive precursors which are converted into an active form, which in turn activates the next clotting factor in sequence, i.e., proenzyme Factor XII is converted to its enzyme XIIa which in turn converts the zymogen Factor XI to the enzyme Factor XIa, which then activates Factor IX, in the presence of calcium. The enzyme Factor IXa in the presence of Factor VIII and phospholipid activates Factor X. This reaction is greatly increased by the prior exposure of Factor VIII to thrombin or Factor Xa.

In the extrinsic pathway, Factor X can be activated by either a complex of thromboplastin and Factor VII, or a complex of platelet phospholipid activated Factor IX and Factor VIII. Activated Factor X, in the presence of calcium, Factor V and platelet phospholipid activates Factor II (prothrombin) which is cleaved to form thrombin which converts Factor I (fibrinogen) to fibrin in blood plasma.

The process of blood coagulation is modified by a number of positive and negative feed back loops and by interaction between these pathways. For example, thrombin and Factor Xa, formed either by activation of the intrinsic or extrinsic pathway, feed back to activate Factor VIII and Factor V. Factor Xa feeds back to initially increase and then to inhibit its own activation by Factor VIIa. The intrinsic and extrinsic pathways are also linked. For example, Factor VII is activated by Factor IXa, XIIa and XIa and Factor VIIa can activate Factor IX.

The basis of in vitro coagulation testing has been the determination of the increase in turbidity or viscosity of a sample, caused by the conversion of fibrinogen to fibrin during clot formation. The screening tests for coagulation disorders include the prothrombin time (PT) and the activated partial thromboplastin time (APTT). Essentially, the screening tests for coagulation disorders are designed to detect a significant abnormality in one or more of the clotting factors and to localize this abnormality to various steps in the coagulation pathway. For example, APTT measures coagulation factors of the intrinsic pathway, including Factors XII, XI, IX, VIII, X, V, II and I which may be abnormal based on heredity or heparin therapy. APTT is therefore useful as a presurgical screen and for monitoring heparin therapy.

The APTT is performed by adding an activator such as kaolin, ellagic acid, or silica, for example, with phospholipid to plasma. This activates Factors XII and XI. Phospholipid substitutes for platelet in the activation of Factor VIII by Factors IX, VIII and V. Blood coagulation is initiated in this clotting test by adding calcium. Factor VII is the only factor not affected by the partial thromboplastin time and the APTT is, therefore, normal in patients with a Factor VII deficiency.

The prothrombin time (PT) test is performed by adding tissue thromboplastin with calcium to plasma. This initiates clotting by activating Factor VII which in turn activates Factor X which in the presence of Factor V, converts prothrombin to thrombin and the thrombin which is so produced converts fibrinogen to fibrin. PT therefore bypasses the intrinsic clotting pathway and is normal in patients with deficiencies of Factors XII, XI, IX and VIII. PT is abnormal in patients with deficiencies of Factors VII, X, V, prothrombin or fibrinogen.

As a result, substantial efforts have been made to measure these clotting components. Most methodologies rely upon immunologic and clotting techniques although clearly the latter is preferred. The immunologic techniques, although generally capable of precisely defining the levels of the various components within the blood stream, are incapable of distinguishing between active and inactive forms. Accordingly, the immunologic methods are felt to be less accurate with respect to the patient's actual clotting ability. Consequently, the results obtained by clotting techniques are preferred as being more clinically significant.

The human eye was the first clot detection system used for coagulation testing, e.g., a normal sample produces a strong gel clot; samples producing thin, watery, webby-type clots are indicative of some coagulation abnormality. Automated coagulation instrumentation, both mechanical and optical density-based, provide data about the end point of the clotting times in the various coagulation tests, e.g., PT and APTT. Typically, most instruments detect the formation of a clot by monitoring either optical turbidity or electrical conductivity. The latter represents the traditional approach employed by the so-called fibrometer-type of instrument. Effectively, this instrument measures increasing conductivity which may be correlated to the formation of clots. Similarly, turbidity may be optically sensed by the decrease in light transmission due to the formation of a clot. Certainly with the normal PT or APTT tests, these methods have found widespread acceptance despite the fact that each test has associated therewith a level of indefiniteness regarding the point at which the clot is determined to have occurred.

A more advanced instrument, such as the Koagu-Lab® (Ortho Diagnostic Systems Inc., Raritan, N.J.) generates a printed graph of the clotting reaction. Clinicians can tell by the shape of the curve generated whether or not the clotting times is reliable, thus providing a stronger information base for their therapeutic decisions. A graph which plots turbidity against reaction time is referred to as "clot signature". As used in the KoaguLab® system, the total turbidity change attached at the maximum clotting endpoint is "delta", the reaction rate of the observed clot formation is Velocity, and the derivative of Velocity or the maximum acceleration of observed clot formation is Acceleration. KoaguLab® may be used to perform PT and APTT assays. These are performed be adding brain thromboplastin or activated partial thromboplastin and calcium chloride respectively, to a plasma sample and determining the time at which the clot forms. Reagents useful for these purposes include, for instance, Ortho Quantitative Fibrinogen Assay (Q.F.A.), Ortho Q.F.A. Thrombin (Human), Ortho Q.F.A. Buffer, Ortho Activated PTT Reagent, Ortho Activated Thrombofax™ Reagent, Ortho Brain Thromboplastin, Fibrindex™ Thrombin, Ortho Plasma Coagulation Controls (obtainable from Ortho Diagnostic Systems Inc., Raritan, N.J.). These materials are accompanied by procedural instructions regarding their use, the relevant portions of which are incorporated herein by reference. Either of the two generalized embodiments of the methods of the present invention may be utilized for calculating PT or APTT coagulation times.

The clot signature essentially adds a qualitative fibrinogen measurement to the standard PT and APTT tests, which may prove useful in detecting certain disease states, including hypercoagulability.

SUMMARY OF THE INVENTION

A method of determining levels of extrinsic and intrinsic clotting factors and protein C is provided. The reaction rate of the observed clot formation or Velocity in a prothrombin time factor-based assay (PT) or an activated partial thromboplastin time factor-based assay (APTT) is determined for both test and normal plasma samples and the reaction rates compared.

In another embodiment of this invention, the first derivative of the reaction rate of the observed clot formation or Acceleration is determined for both test and normal plasma samples and the results are compared.

In the present invention, it was surprisingly found that Velocity (the reaction rate of the observed clot formation), and Acceleration (the derivative of Velocity or the maximum acceleration of observed clot formation) are useful indicators for quantitating the various clotting factors and protein C. The "clot signature" (turbidity versus reaction time) therefore becomes a useful clinical tool for monitoring drug therapy (e.g., heparin or coumarin) and provides useful information concerning diagnosis and treatment of disorders such as liver disease, hemophilia, protein C deficiency or DIC.

Accordingly, the present invention provides a method of determining levels of extrinsic and intrinsic clotting factors and protein C. This and further objects of the present invention will become apparent from the following more detailed description.

DESCRIPTION OF THE DRAWINGS

FIG. 8 is the clot signature information for three DIC samples generated by a KoaguLab® device, depicting turbidity versus time for a PT (left hand signature) assay for each of three patients.

DETAILED DESCRIPTION OF THE INVENTION

Figure 1:
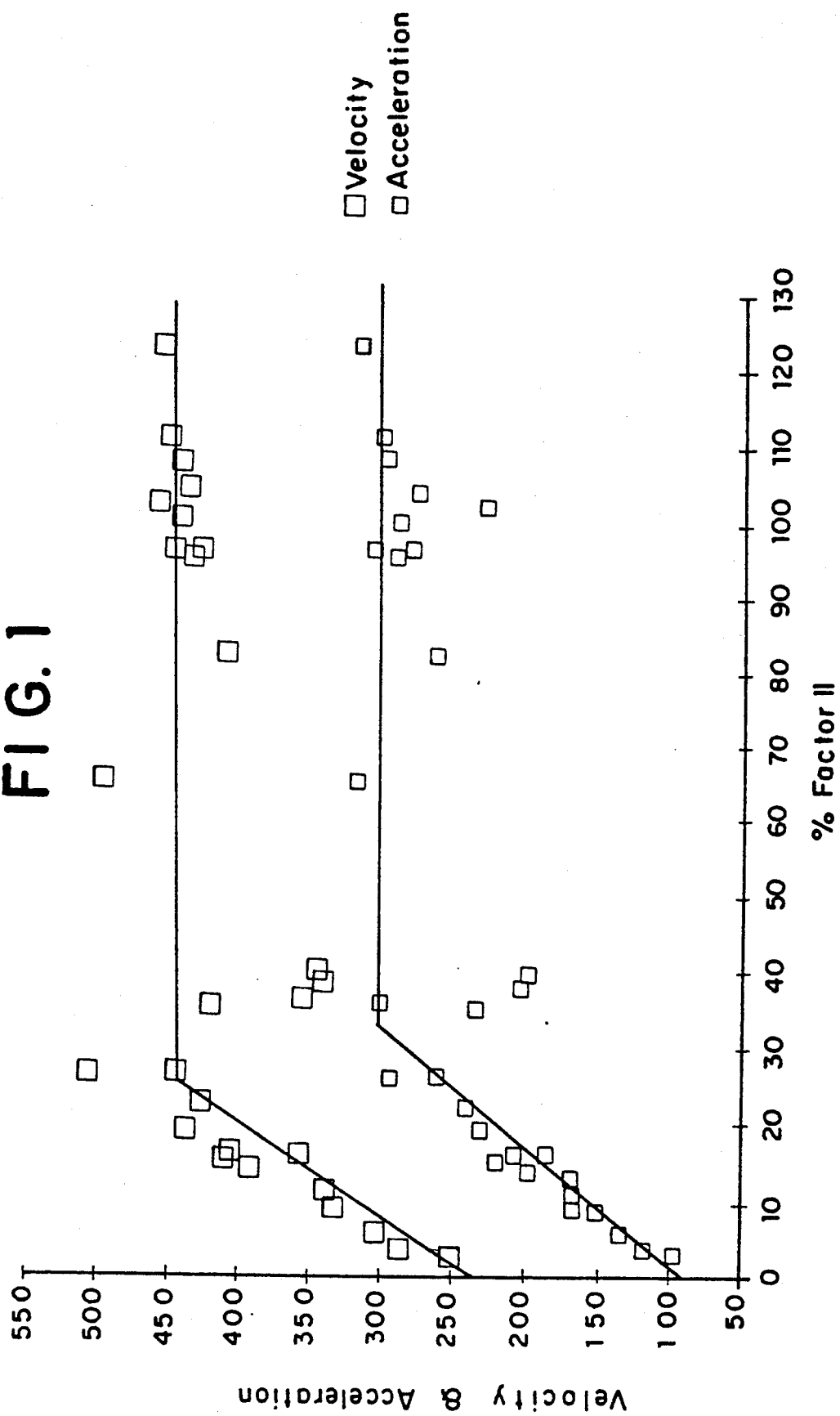
FIG. 1 is a graph showing the correlation of Factor II levels with Factor II Velocity and acceleration.

The present invention provides a method to determine levels of extrinsic and intrinsic clotting factors and protein C using PT or APTT factor-based assays and the observed rate of clot formation (Velocity) and the first derivative of the observed rate of clot formation (Acceleration) determined in test samples and compared with normal plasma samples. The comparisons can be made in several ways. The Velocity or Acceleration value in the test sample can be compared directly with the Velocity or Acceleration value in a normal plasma sample or an individual factor level can be correlated with that factor's Velocity and Acceleration in a test sample, which is compared with known, normal ranges.

A prothrombin time test (PT) is used to determine deficiencies of clotting factor activity in the extrinsic pathway. By adding tissue thromboplastin, e.g., ORTHO Brain Thromboplastin, to normal anticoagulated plasma, the clotting mechanism is initiated. The endpoint of the assay procedure is the appearance of a solid gel clot, which may be determined visually, mechanically, or by optical means. If there is a deficiency of factor activity in the extrinsic pathway, the time required for clot formation will be prolonged beyond that expected for normal plasma. Clotting times on patient plasma samples are compared with normal plasma samples. In this invention, the reaction rate of the observed rate of clot formation (Velocity) and the first derivative of the observed rate of clot formation (Acceleration) in a factor-based PT assay are determined in test samples and compared with normal plasma samples.

An activated partial thromboplastin time test (APTT) is used to indicate abnormalities in most of the procoagulant clotting factors. The APTT assay is a useful sensitive procedure for generating heparin response curves and for screening deficiencies of clotting factors in the intrinsic pathway. In this invention, activated THROMBOFAX (manufactured by ORTHO Diagnostic Systems Inc., Raritan, N.J.), a buffered reagent which contains phospholipids and a plasma activator, is mixed with test plasma and a specific intrinsic factor deficient plasma. The clotting reaction is initiated by the addition of ionic calcium and the test result is the time required for clot formation.

In one embodiment of this invention, the reaction rate of the observed clot formation, or Velocity, in a factor-based PT or APTT assay is determined for both test and normal plasma samples and the Velocity values compared. This method involves determining the reaction rate of the observed clot formation in a normal plasma sample, determining the reaction rate of the observed clot formation in a test plasma sample, and then comparing the reaction rate determined in the test sample with the reaction rate determined in a normal plasma sample.

In another embodiment of this invention, the first derivative of the reaction rate of the observed clot formation, or Acceleration, in a factor-based PT or APTT assay is determined for both test and normal plasma samples and the values compared. The method involves determining the first derivative of the reaction rate of the observed clot formation in a normal plasma sample, determining the first derivative of the reaction rate of the observed clot formation in a test plasma sample, and comparing the first derivative determined in the test sample with the first derivative determined in the normal plasma sample.

The methods of the invention can be used to determine levels of extrinsic and intrinsic clotting factors and protein C. It is also useful for determining levels of extrinsic clotting Factors II, VII and X for monitoring coumarin therapy. In an embodiment of this invention, levels of extrinsic clotting Factors II, VII, and X for monitoring coumarin therapy is provided. A factor-based PT assay is performed to measure said extrinsic clotting factors. The Velocity is determined and compared with the reaction rate observed in normal plasma samples. In another embodiment, the first derivative of the observed clot formation is determined for both test and normal plasma samples, and the results compared.

The method is also useful for determining levels of intrinsic clotting Factors XII, XI, IX, VIII, V, X and II for monitoring heparin therapy. In another embodiment, a method of determining levels of intrinsic clotting Factors XII, XI, IX, VIII, V, X, and II is provided. A factor-based APTT assay is performed and the reaction rate of observed clot formation is determined and compared with the reaction rate observed in normal plasma samples. In another embodiment, the Acceleration is determined for both test and normal plasma samples, and the results compared.

Individual clotting factors can also be determined in accordance with this method. Individual intrinsic or extrinsic clotting factors are determined by performing a PT or APTT assay using a specific factor deficient plasma, determining the reaction rate of observed clot formation in a normal plasma sample mixed with said factor deficient plasma, determining the observed rate of observed clot formation in a test sample mixed with said factor deficient plasma, and comparing the Velocity values obtain. In another embodiment, the first derivative of the reaction rate of observed clot formation is determined for a test sample and compared with the value for a normal plasma sample, where both samples are mixed with the specific factor deficient plasma.

Protein C levels are also determined in accordance with the teachings of this method by performing a modified APTT assay by activating the protein C with a protein C activator, such as snake venom. The reaction rate of the observed clot formation in a test sample mixed with protein C deficient plasma is compared with the Velocity determined in a normal plasma sample. The prolongation of the clotting time is proportional to the amount of protein C in the test plasma sample.

Figure 2:
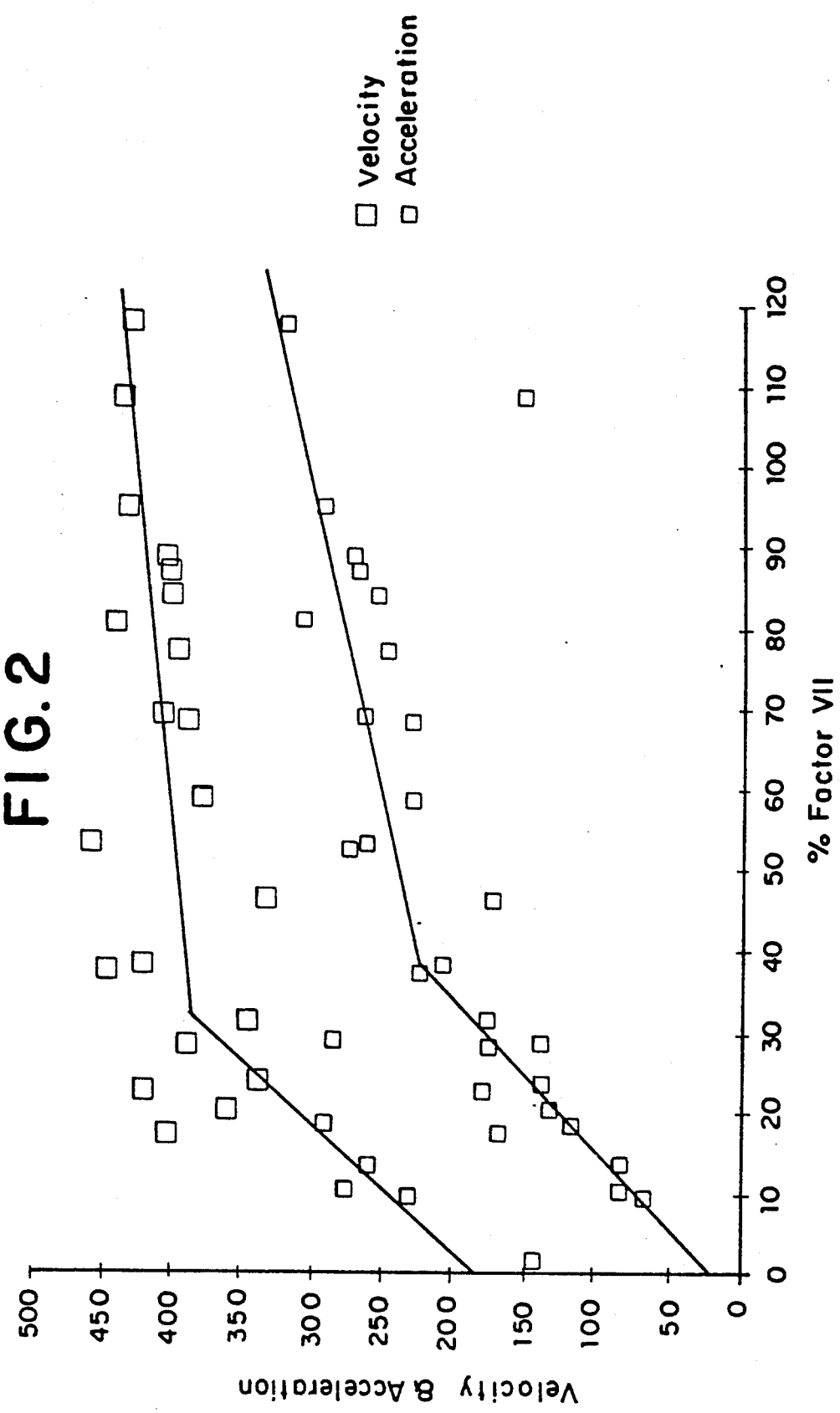
FIG. 2 is a graph showing the correlation of Factor VII level to Factor VII Velocity and Acceleration.
Figure 3:
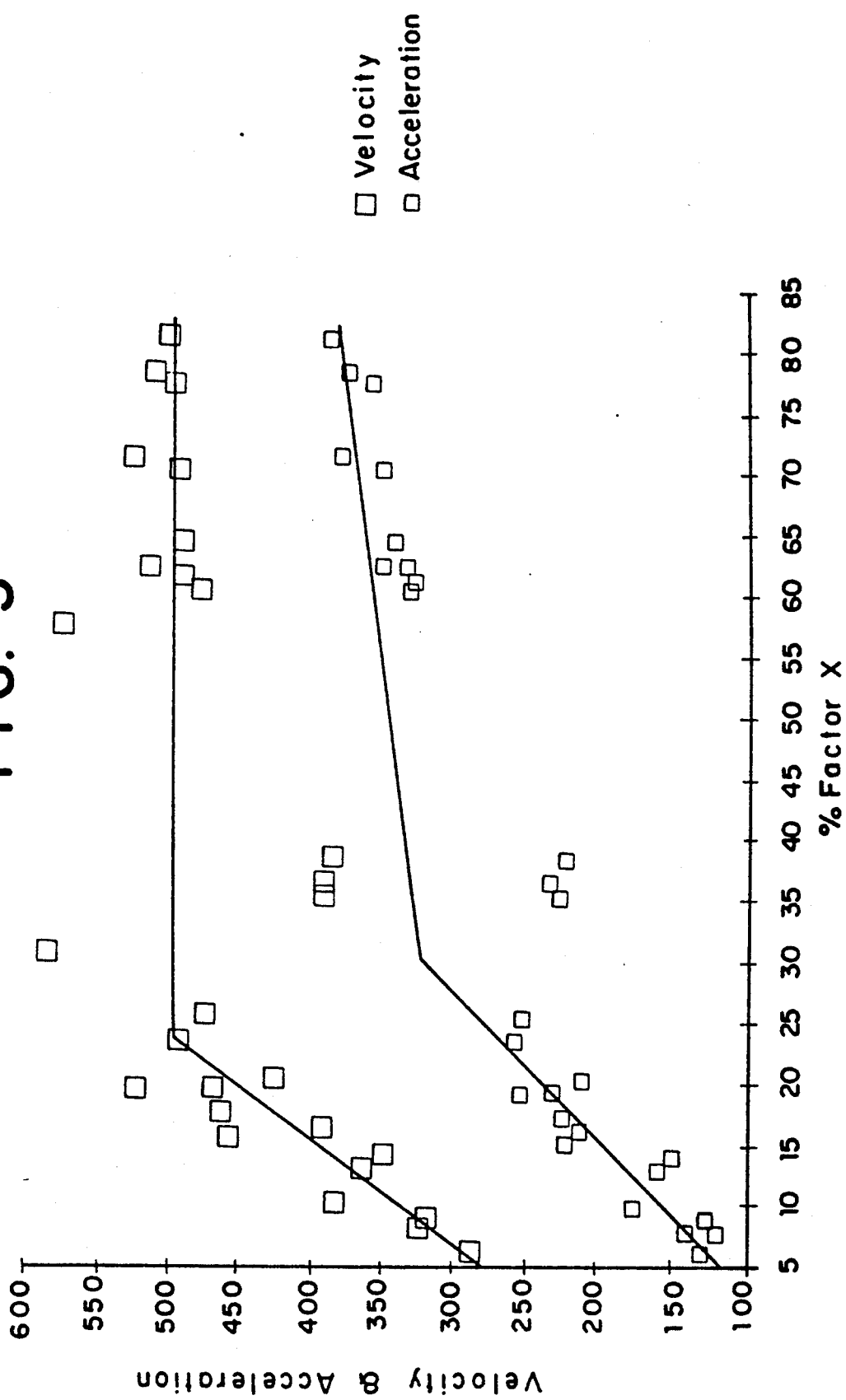
FIG. 3 is a graph showing the correlation of Factor X concentration with Factor X Velocity and Acceleration.
Figure 4:
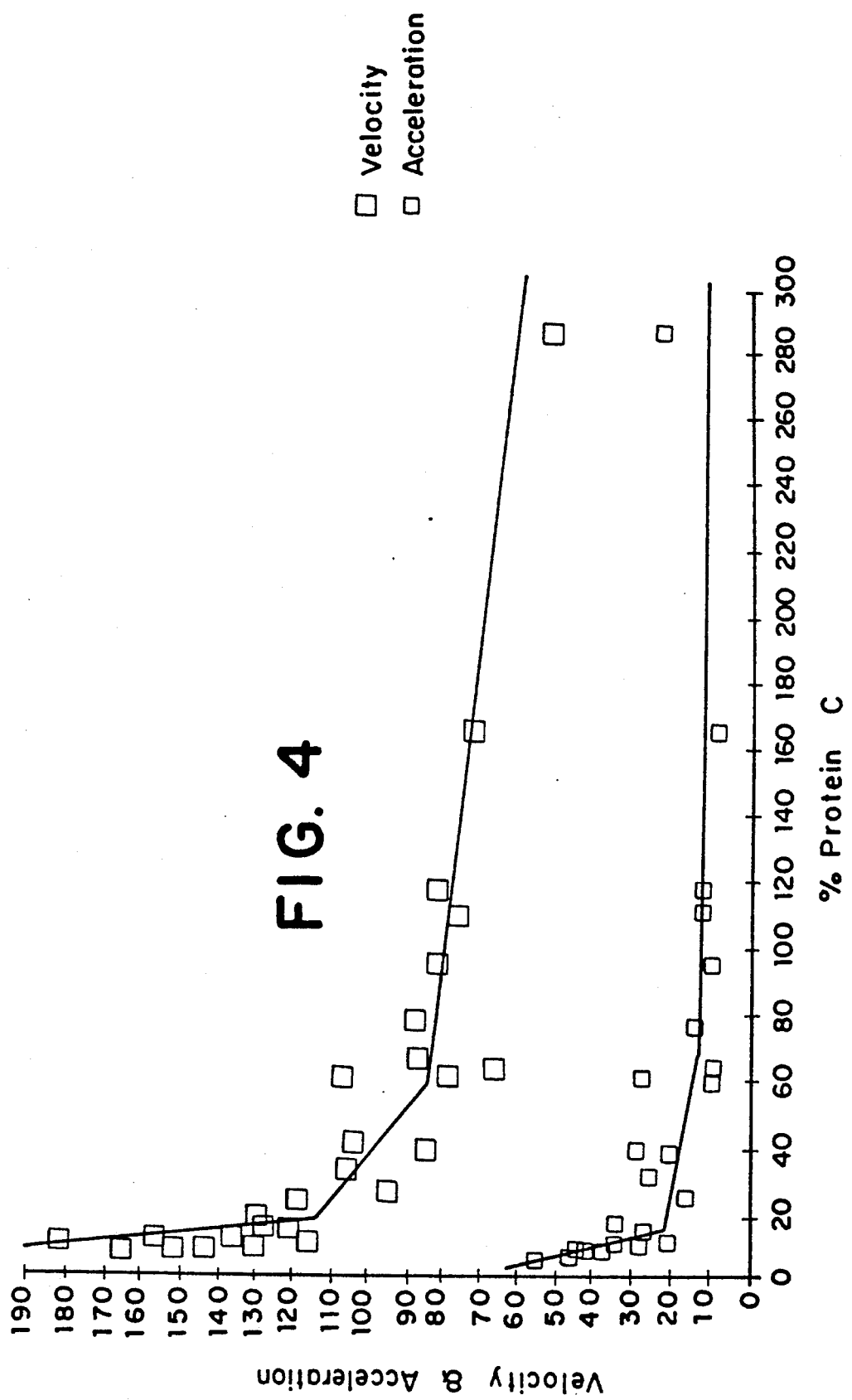
FIG. 4 is a graph showing the correlation of protein C concentration with protein C Velocity and Acceleration.

Abnormal clotting factors and protein C are identified by the method of this invention by determining the Velocity and Acceleration values for a test sample and normal plasma and then correlating the level of the clotting factor with Velocity and Acceleration. An example of the correlation of Factor II levels with Factor II Velocity and Acceleration, according to this method is shown in FIG. 1, FIG. 2 depicts an example of the correlation of Factor VII levels to Factor VII Velocity and Acceleration. In FIG. 3, a correlation of Factor X concentration with Factor X Velocity and Acceleration is shown. FIG. 4 depicts an example of the correlation of protein C concentration with protein C Velocity and Acceleration in accordance with this method.

The invention is further illustrated by means of the following examples. These examples are meant to be illustrations only and are not intended to limit the present invention to the specific embodiments.

EXAMPLE 1

PT and APTT Clot Signature Data For 20 Normal Volunteers

The ranges for clot signature data obtained in PT and APTT assays with fresh normal patient samples are listed below:

|  | PT | APTT |
|---|---|---|
| Clotting Time | 11.7–13.9 | 30.1–35.5 |
| Delta | 1867–3539 | 2919–3644 |
| Velocity | 503–1092 | 299–553 |
| Acceleration | 404–861 | 115–301 |

EXAMPLE 2

PT clot signature For Patients Undergoing Coumarin Oral Anticoagulant Therapy

The clot signature therapy for four patients undergoing coumarin therapy were:

|  | PT |
|---|---|
| Clotting Time | 15.3–24.6 |
| Delta | 1841–3548 |
| Velocity | 245–727 |

-continued

| | PT |
|---|---|
| Acceleration | 101–397 |

When these clot signatures are compared with those of normal PTs, the steepness of the curve is lower as reflected in the velocity and acceleration values. The delta values for the coumarin samples are about the same as those found with normal plasma, which is expected because the delta value correlates with fibrinogen, which is not affected by coumarin. The clotting Factors II, VII and X are affected by coumarin and consequently, the rate of clot formation is more reflective of the different levels of the clotting factors. The velocity range found with normal patient samples was 503 to 1092. The velocity values with coumarin samples ranged from 245 to 727, which is low normal to below normal. The clot signature could therefore be useful to indicate whether a patient was receiving too much or too little coumarin to ensure that clot formation would be lessened.

EXAMPLE 3

APTT Clot Signature Data in In Vitro Heparinized Patient Samples

The clot signature data for three patients undergoing heparin anticoagulant therapy were:

| | APTT |
|---|---|
| Clotting | 45.6–104 |
| Delta | 1185–3711 |
| Velocity | 142–514 |
| Acceleration | 11–186 |

The clot signature in this case is a useful tool to alert the lab immediately when a longer maximum end point is required. Many patients on heparin therapy have higher than normal fibrinogen levels. For this reason, the delta value is a better indicator of fibrinogen levels.

Low velocity values for these patients may indicate a reduced reaction rate of clot formation indicating that a patient may be receiving too high a dose of heparin and could experience clinical bleeding, especially if additional heparin is administered. On the other hand, a high velocity value indicates a rapid rate of clot formation. A patient such as this requires additional heparin or may be reflecting a resistance to heparin. If administration of additional heparin reduces the patient's velocity value, the clinician would be able to monitor the patient by balancing the APTT clotting time with the velocity value.

EXAMPLE 4

PT/APTT Slot Signatures for Patients with Confirmed Liver Disease

Figure 5:
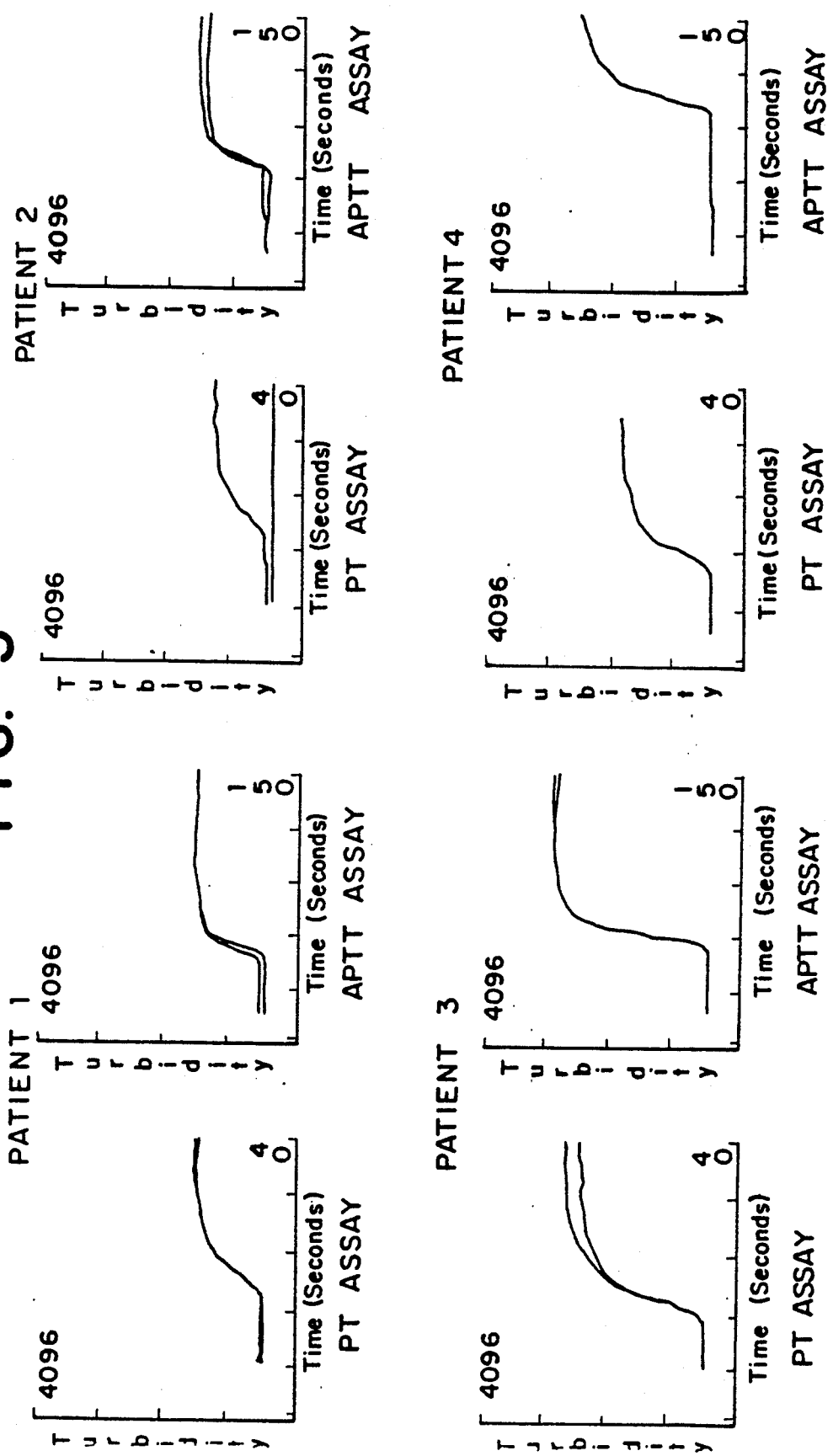
FIG. 5 is the clot signature information for four patients with liver disease. The "clot signature" is a graphical depiction of turbidity versus time (seconds) as generated by a KoaguLab® device. The left hand signature for each patient indicates the results of a PT assay. The right hand signature, an APTT assay.

FIG. 5 compares the PT and APTT clot signature information for four patients with liver disease. The four patients are obviously quite different just from a cursory glance at the clot signatures. The delta values indicate that patient 3 had a normal fibrinogen level, whereas patients 1 and 2 have low fibrinogen levels. Patient 4 is probably at a low normal fibrinogen level. From the PT Velocity values, patients 1 and 2 appear to have low concentrations of one or more of the Factors V, X, VII and II, whereas patients 3 and 4 appear to have low normal levels. From the APTT Velocity values, patients 1 and 2 appear to have low levels of one or more Factors XII, XI, V, VIII, II, IX and X levels, whereas patients 3 and 4 exhibit normal levels. The prolonged APTT clotting times for patients 3 and 4 were due to heparin rather than abnormally low levels of factors, since the APTT Velocity values do not indicate abnormally low clotting factors. The analyses provided for these four patients with confirmed liver disease were as follows:

| Patient | F II | F VIII | FIX | FX | AT III |
|---|---|---|---|---|---|
| 1 | 36% | 914% | — | 38% | 28% |
| 2 | 28% | 702% | 36% | 47% | 38% |
| 3 | 47% | 280% | 33% | 76% | 30% |
| 4 | 58% | 926% | 43% | 66% | 30% |

EXAMPLE 5

PT/APTT Clot Signatures for Patient with Hemophilia (Factor VIII less than 1%)

Figure 6:
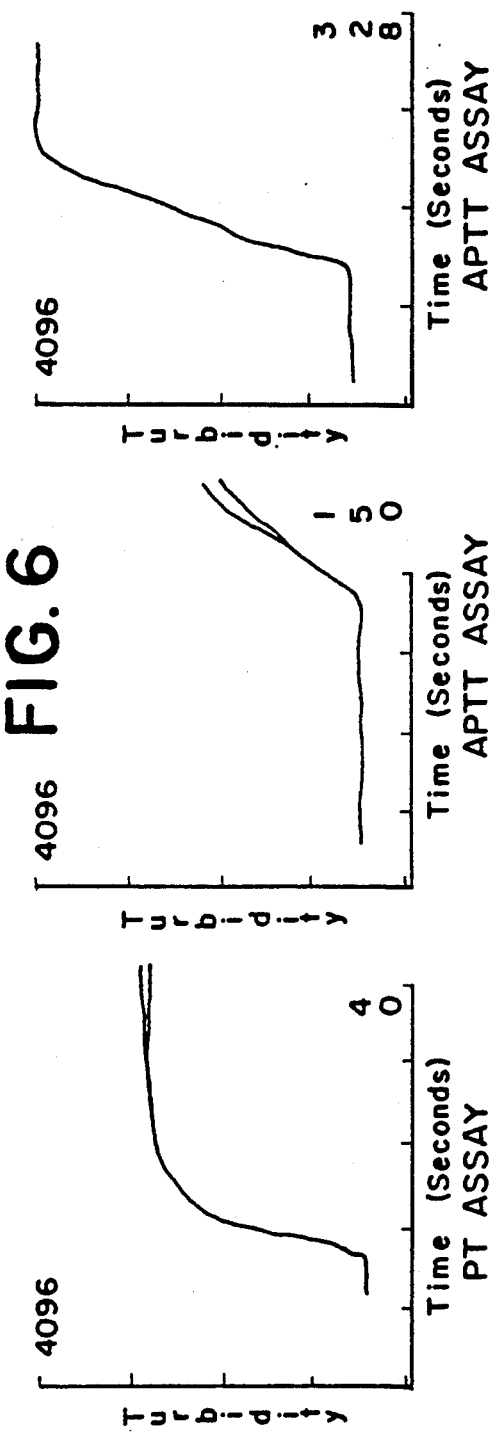
FIG. 6 is the clot signature information for a hemophilia A patient's sample, Factor VIII less than 1%, generated by a KoaguLab® device, depicting turbidity versus time (seconds) for a PT (left hand signature) and APTT (right hand signature) assay.

The PT and APTT clot signatures for a hemophilia A patient's sample, Factor VIII less than 1%, is illustrated in FIG. 6. The PT clot signature appears to be normal. The Velocity and Acceleration values suggest that the prolonged APTT time was caused by a factor deficiency or an inhibitor. The clinical history of the patient would assist the laboratory in selecting what tests should be performed next to identify the cause of the prolonged APTT clotting time.

EXAMPLE 6

PT/APTT Clot Signatures for a Patient with Protein C Deficiency

Figure 7:
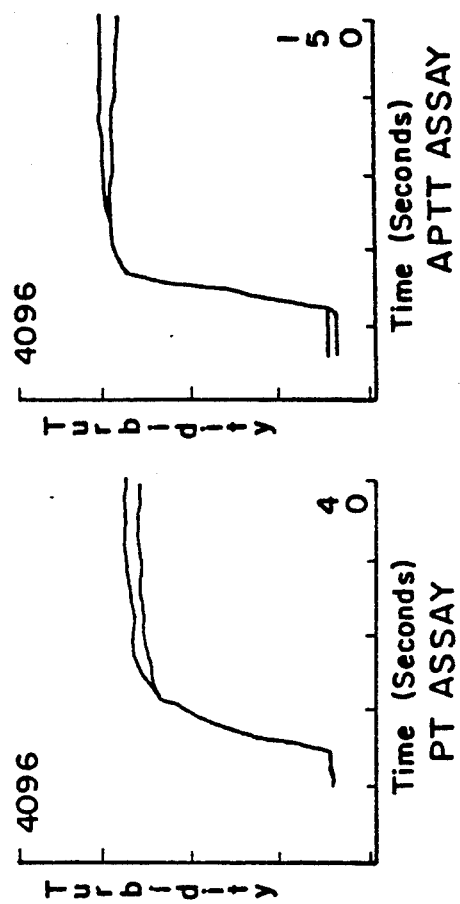
FIG. 7 is the clot signature information from a protein C deficient plasma, generated by a KoaguLab® device, depicting turbidity versus time for a PT (left hand signature) and APTT (right hand signature) assay.

The PT and APTT clot signature information from a Protein C deficient patient does not appear to differ from that obtained with a normal plasma as shown in FIG. 7. One would not anticipate that the Protein C deficiency sample would have abnormal PT and APTT clotting reactions, unless the patient experienced some external trauma.

EXAMPLE 7

PT/APTT Clot Signatures for Three Patients with DIC

The last example presented is the clot signatures for three DIC samples as shown in FIG. 8. The clot signatures suggest that patients 21 and 22 have low fibrinogen levels as indicated by the PT Delta values (left hand signature). Patient 23 appears to have a low normal fibrinogen level from the PT Delta value. The rate of clot formation as indicated by Velocity values in both the PT and APTT clot signature data for patients 21 and 22 indicated significantly lower than normal Velocity value. This suggests that these two patients are in a critical state in contrast to patient 23. Patient 23 is either on the road to recovery or just about to enter a crisis. The significance of the clot signature is just beginning to emerge, but already there are indications that it can assist the clinical laboratory to gain valuable insight into a fuller clinical understanding of the patient's hemostatic state.

As seen from the above, a simple reproducible method for determining levels of extrinsic and intrinsic clotting factors and protein C is provided.

While the foregoing description has been directed to the preferred embodiments of the present invention, those of ordinary skill in the art in this field will appreciate that various modifications can be made in the materials and methods described herein without departing from the scope of the present invention, which is described more particularly in the claims appended hereto.

What is claimed:

1. A method of determining levels of extrinsic and intrinsic clotting factors and protein C in a test plasma sample, said method comprising the steps of:
    determining the rate of clot formation in a normal plasma sample;
    determining the rate of clot formation in said test plasma sample; and
    comparing said rate of clot formation determined in said test plasma sample with said rate of clot formation determining in said normal sample in order to determine levels of extrinsic and intrinsic clotting factors and protein C.

2. A method of determining relative levels of extrinsic clotting Factors II, VII, and X in a test sample for monitoring coumarin therapy, said method comprising the step of:
    performing a prothrombin time test on said test sample to measure said extrinsic clotting factors;
    determining the rate of clot formation in a normal plasma sample;
    determining the rate of clot formation in said test sample based on said prothrombin time test; and
    comparing said rate of clot formation determined in said test sample with said clot formation determined in said normal sample in order to determine the relative levels of extrinsic clotting Factors II, VII, and X.

3. A method of determining intrinsic clotting Factors XII, XI, IX, VIII, V, X and II in a test sample for monitoring heparin therapy, said method comprising the steps of:
    performing an activated partial thromboplastin time test on said test sample to measure said intrinsic clotting factors;
    determining the rate of clot formation in a normal plasma sample;
    determining the rate of clot formation in said test sample based on said activated partial thromboplastin time test; and
    comparing said rate of clot formation determined in said test sample with said rate of clot formation determined in said normal sample in order to determine intrinsic clotting Factors XII, XI, IX, VIII, V, X and II.

4. A method of determining the level of a specific intrinsic clotting factor in a test sample, said method comprising the steps of:
    performing an activated partial thromboplastin time test on said test sample mixed with specific factor deficient plasma;
    determining the rate of clot formation in a normal plasma sample mixed with specific factor deficient plasma;
    determining the rate of clot formation in said test sample mixed with specific factor deficient plasma based on said activated partial thromboplastin time test; and
    comparing said rate of clot formation determined in said test sample with said rate of clot formation determined in said normal sample in order to determine the level of a specific intrinsic clotting factor.

5. A method of determining the level of a specific extrinsic clotting factor in a test sample, said method comprising the steps of:
    performing a prothrombin time test on said test sample mixed with specific factor deficient plasma;
    determining the rate of clot formation in a normal plasma sample mixed with specific factor deficient plasma;
    determining the rate of clot formation in said test sample mixed with specific factor deficient plasma based on said prothrombin time test; and
    comparing said rate of clot formation determined in said test sample with said rate of clot formation determined in said normal sample in order to determine the level of a specific extrinsic clotting factor.

6. A method for determining the level of protein C in a test sample, said method comprising the steps of:
    performing a modified activated partial thromboplastin time test on said test sample mixed with protein C deficient plasma;
    determining the rate of clot formation in a normal plasma sample mixed with protein C deficient plasma;
    determining the rate of clot formation in a test sample mixed with protein C deficient plasma based on said modified activated partial thromboplastin time test; and
    comparing said rate of clot formation determined in said test sample with said rate of clot formation determined in said normal sample in order to determine the level of protein C.

7. The method of claim 6 wherein the step of performing the modified activated partial thromboplastin time test is performed by activating said protein C with a protein C activator.

8. The method of claim 7 wherein said protein C activator is snake venom.

9. A method of identifying abnormal extrinsic clotting factor levels in a test sample, said method comprising the steps of:
    performing a prothrombin time test on said test sample to measure a clotting factor level in said test sample;
    determining the rate of clot formation of said test sample based on said prothrombin time test;
    determining a first derivative of the rate of clot formation based on said prothrombin time test; and
    correlating the measured clotting factor level with the determined rate of clot formation and the determined first derivative in order to identify abnormal extrinsic clotting factor levels.

10. The method of claim 9 wherein the result of the step of measuring the level of said clotting factor is expressed as a percentage of said clotting factor.

11. A method of identifying abnormal intrinsic clotting factor levels in a test sample, said method comprising the steps of:
    performing an activated partial thromboplastin time test on said test sample to measure a clotting factor level in said test sample;
    determining the rate of clot formation of said test sample based on said activated partial thromboplastin time test;
    determining a first derivative of the rate of clot formation based on said activated partial thromboplastin time test; and correlating the measured clotting factor level with the determined rate of clot formation and the determined first derivative in order to identify abnormal intrinsic clotting factor levels.

12. The method of claim 11 wherein the result of the step of measuring the level of said clotting factor is expressed as a percentage of said clotting factor.

13. A method of identifying abnormal protein C levels in a test sample, said method comprising the steps of;

performing a modified activated partial thromboplastin time test on said test sample to measure a protein C level;

determining the rate of clot formation of said test sample based on said activated partial thromboplastin time test;

determining a first derivative of the rate of clot formation based on said activated partial thromboplastin time test; and correlating the measured protein C level with the determined rate of clot formation and the determined first derivative in order to identify abnormal protein C levels.

14. The method of claim 11 wherein the result of the step of measuring the level of said protein C is expressed as a percentage of said protein C.

15. A method according to claim 9, 10, 11, 12 or 13 wherein the step of correlating comprises plotting said measured level with said determined rate of clot formation and said determined first derivative.

16. A method according to claim 9, 10, 11, 12 or 13 wherein said step of correlating comprises providing the results of the correlation of said measured level with said determined rate of clot formation and said determined first derivative in a graph.

17. A method according to claim 15, further comprising the step of analyzing a plot resulting from said step of plotting, wherein said abnormal level is determined from said analysis.

18. A method according to claim 16, further comprising the step of analyzing said graph, wherein said abnormal level is determined from analysis of said graph.

* * * * *

UNITED STATES PATENT AND TRADEMARK OFFICE
CERTIFICATE OF CORRECTION

PATENT NO. : 5,169,786

DATED : December 8, 1992

INVENTOR(S) : James J. Carroll and Stephen M. Autenrieth

It is certified that error appears in the above-identified patent and that said Letters Patent is hereby corrected as shown below:

Column 9, Line 19 - (under Claim 1) "determining" should be typed as "determined".

Signed and Sealed this

Twenty-third Day of November, 1993

Attest:

BRUCE LEHMAN

Attesting Officer

Commissioner of Patents and Trademarks